(12) United States Patent
Resconi et al.

(10) Patent No.: US 7,002,031 B2
(45) Date of Patent: Feb. 21, 2006

(54) PREPARATION OF SILICON-BRIDGED METALLOCENE COMPOUNDS

(75) Inventors: Luigi Resconi, Ferrara (IT); Simona Guidotti, Casalecchio di Reno-Bologna (IT); Davide Balboni, Ferrara (IT)

(73) Assignee: Basell Polyolefine GmbH, Wesseling (DE)

( * ) Notice: Subject to any disclaimer, the term of this patent is extended or adjusted under 35 U.S.C. 154(b) by 21 days.

(21) Appl. No.: 10/500,542

(22) PCT Filed: Dec. 30, 2002

(86) PCT No.: PCT/EP02/14899

§ 371 (c)(1),
(2), (4) Date: Jun. 30, 2004

(87) PCT Pub. No.: WO03/057705

PCT Pub. Date: Jul. 17, 2003

(65) Prior Publication Data

US 2005/0080244 A1    Apr. 14, 2005

(30) Foreign Application Priority Data

Jan. 8, 2002 (EP) .................... 02075040

(51) Int. Cl.
*C07F 17/00* (2006.01)
*B01J 31/00* (2006.01)

(52) U.S. Cl. .................. 556/11; 556/12; 534/15; 502/103; 502/117; 526/943; 987/2

(58) Field of Classification Search .................. 556/11, 556/12; 534/15
See application file for complete search history.

(56) References Cited

U.S. PATENT DOCUMENTS 5,770,753 A * 6/1998 Kuber et al. .................. 556/11
5,786,432 A * 7/1998 Kuber et al. .................. 526/127
6,051,727 A * 4/2000 Kuber et al. .................. 556/11
6,162,937 A * 12/2000 Dang et al. .................... 556/87
6,191,294 B1 * 2/2001 Resconi et al. ............... 556/11
6,242,544 B1 * 6/2001 Kuber et al. .................. 526/127
6,255,506 B1 * 7/2001 Kuber et al. .................. 556/11
6,268,518 B1 * 7/2001 Resconi et al. ............... 556/43

FOREIGN PATENT DOCUMENTS

| EP | 0576970 | 1/1994 |
|----|---------|--------|
| EP | 0604908 | 7/1994 |
| WO | 9936427 | 7/1909 |
| WO | 9619488 | 6/1996 |
| WO | 9843989 | 10/1998 |

OTHER PUBLICATIONS

D. Balboni et al., "Group 4 Dimethylmetallocenes: Improved Synthesis and Reactivity Studies;" *Inorg. Chem.*, vol. 40, p. 6588-6597 (2001).

* cited by examiner

*Primary Examiner*—Porfirio Nazario-Gonzalez

(57) ABSTRACT

A process for obtaining silicon-bridged metallocene compounds comprising the following steps:
a) reacting, at a temperature of between −10° C. and 70° C., the starting ligand with about 2 molar equivalents of an alkylating agent;
b) after the reaction has been completed, adding at least 2 molar equivalents of an alkylating agent that can be also different from the first one; and
c) reacting, at a temperature of between −10° C. and 70° C., the product obtained from step b) with at least 1 molar equivalent of a compound of formula $ML'_s$, wherein M is a transition metal; s is an integer corresponding to the oxidation state of the metal; and L' is an halogen atom selected from chlorine, bromine and iodine.

10 Claims, No Drawings

PREPARATION OF SILICON-BRIDGED METALLOCENE COMPOUNDS

The present invention relates to a process, for the preparation of silicon-bridged metallocene compounds. These metallocenes are useful as catalyst components, e.g. in the polymerization, oligomerization and hydrogenation of olefins, in association with alumoxanes and/or compounds able to form alkylmetallocene cations. Homogeneous catalytic systems based on metallocenes in association with an aluminum alkyl compound or an alumoxane are well known in the state of the art and are widely used in the polymerization reactions of olefins. When the sigrna ligands of the central metal atom are alkyl or aryl groups, the above metallocenes are usually obtained according to a process comprising the following steps:

1) preparing the metallocene dihalide, usually the metallocene dichloride, by reacting suitable ligand/s with $MX_4$, wherein X is halogen (usually $TiCl_4$ or $ZrCl_4$);
2) converting the metallocene dihalide obtained in step (1) into the corresponding dialkyl or diaryl complex, by substitution of the halogens linked to the metal atom with the desired alkyl or aryl groups, by means of an alkylating agent such as alkyllithium, dialkylmagnesium or the corresponding Grignard reagent.

Nevertheless, the above metallocenes can not be expediently synthesized by the existing methodology; in fact, prior art processes imply always the synthesis of the metallocene dihalide, that is subsequently transformed into the target product, thus leading to unsatisfactory total yields and requiring at least two process steps.

WO 99/36427 discloses a process for the preparation of a dialkyl or monoalkyl metallocene compounds that comprises the following steps:
1. contacting the cyclopentadienyl ligand with at least 4 equivalents of an alkylating agent; and
2. contacting the reaction mixture with a metal halide of formula $MX_4$, wherein X is halogen (usually $TiCl_4$ or $ZrCl_4$).

WO 99/36427 identifies four temperature ranges for the four different phases of the process, secifically:
phase 1) the addition of the alkylating agent is carried out within a preferred temperature range of from −80° C. to −20° C.;
phase 2) the alkylating agent is allowed to react within a preferred temperature range of from −10° C. to +80° C.; more preferably at room temperature;
phase 3) the addition of the metal halide is done within a preferred temperature range of from −80° C. to −70° C.; and
phase 4) the metal halide is allowed to react within a preferred temperature range of from −50° C. to 0° C.

In the examples only carbon-bridged metallocenes were synthesized and step 1) was carried out in a single addition of the 4 equivalents of alkylating agent.

The temperatures used in the examples of WO 99/36427 are not of industrial interest. Moreover, as shown in the present comparatives examples, this process, when used for synthesizing silicon-bridged metallocene compounds, gives rise to yields that are not completely satisfactory, and when applied to ligands having a particular structure, gives rise to the formation of monohalyde monoalkyl derivatives as undesirable by-products.

In "Inorganic Chemistry" 2001, 40, 6588–6597 higher temperatures have been used for obtaining carbon bridged metallocene compounds, but the alkylating agent is always added in a single addition. Thus it would be desirable to provide an industrial process that permits to obtain silicon-bridged metallocene compounds in higher yields.

It has now been found that by a proper selection of the temperatures and by adding the alkylating agent in two steps, it is possible to improve the yields of this process. Thus the present invention relates to a process for preparing silicon-bridged metallocene compounds of formula (I):

$$(Cp)(SiR^1{}_2)(Cp)ML_q \qquad (I)$$

wherein $(SiR^1{}_2)$ is a divalent group bridging the two Cp rings, the $R^1$ groups, equal to or different from each other, are hydrogen atoms, or a linear or branched, saturated or unsaturated $C_1$–$C_{20}$ alky, $C_3$–$C_{20}$ cycloalkyl, $C_6$–$C_{20}$ aryl, $C_7$–$C_{20}$ allylaryl or $C_7$–$C_{20}$ arylalkyl group, two $R^1$ can optionally join to form a 3–7 membered ring; Cp, equal to or different from each other, is a substituted or unsubstituted cyclopentadienyl group, optionally condensed to one or more substituted or unsubstituted, saturated, unsaturated or aromatic rings, containing from 4 to 6 carbon atoms, optionally containing one or more heteroatoms; M is a transition metal belonging to group 3, 4, 5, 6 or to the lanthanide or actinide groups of the Periodic Table of the Elements (IUPAC version); the substituents L, equal to or different from each other, are monoanionic sigma ligands selected from the group consisting of linear or branched, saturated or unsaturated $C_1$–$C_{20}$ alky, $C_3$–$C_{20}$ cycloalkyl, $C_6$–$C_{20}$ aryl, $C_7$–$C_{20}$ alkylaryl and $C_7$–$C_{20}$ arylalkyl groups, optionally containing one or more Si or Ge atoms; preferably, the substituents L are the same;

q is an integer ranging from 0 to 2, being equal to the oxidation state of the metal M minus 2; said process comprises the following steps:

a) reacting, at a temperature of between −10° C. and 70° C., a ligand of formula $(Y\text{-}Cp)(SiR^1{}_2)(Cp\text{-}Y)$ with about 2 molar equivalents of an alkylating agent of formula $TH_w$, $L_jB$ or $LMgL'$, wherein Cp, $R^1$, and L have the meaning reported above; T is lithium, sodium or potassium, H is an hydrogen atom, w is 0 or 1, when w is 0 the compound $TH_w$ is metallic lithium, sodium or potassium, when w is 1 the compound of formula $TH_w$ is an hydride of lithium, sodium or potassium, L' is an halogen atom selected from chlorine, bromine and iodine; B is an alkali or alkali-earth metal; and j is 1 or 2, j being equal to 1 when B is an alkali metal, and j being equal to 2 when B is an alkali-earth metal; the groups Y, the same or different from each other, are suitable leaving groups;

b) after the reaction has been completed, i.e. in a time ranging from 1 minute to 6 hours, preferably from 20 minutes to 5 hours, more preferably from 40 minutes to 5 hours, adding at least q molar equivalents, preferably at least 1+q molar equivalents, of an alkylating agent of formula $L_jB$ or $LMgL'$; and c) reacting, at a temperature of between −10° C. and 70° C., the product obtained from step b) with at least 1 molar equivalent of a compound of formula $ML'_s$, wherein M have the meaning reported above; s is an integer corresponding to the oxidation state of the metal and ranges from 3 to 6; and L' is an halogen atom selected from chlorine, bromine and iodine.

In the metallocenes of formula (I), preferably $R^1$ is a hydrogen atom, a methyl or a phenyl radical;
the ligand Cp, which is π-bonded to said metal M, is preferably selected from the group consisting of cyclopentadienyl, mono-, di-, tri- and tetra-methyl cyclopentadienyl; 4-$^t$butyl-cyclopentadienyl; 4-adamantyl-cyclopentadienyl; indenyl; mono-, di-, tri- and tetra-methyl indenyl; 4,5,6,7-tetrahydroindenyl; 2-methyl-indenyl; 2-methyl-4-phenyl-indenyl; 2-isopropyl-4-phenyl-indenyl; 2-methyl-4(4'tert-butyl-phenyl)-indenyl; fluorenyl; 5,10-dihydroindeno[1,2-b]indol-10-yl; N-methyl- or N-phenyl-5,10-dihydroindeno[1,2-b]indol-10-yl; 5,6-dihydroindeno[2,1-b]indol-6-yl; N-methyl-or N-phenyl-5,6-dihydroindeno[2,1-b]indol-6-yl; azapentalene-4-yl; thiapentalene-4-yl; azapentalene-6-yl; thiapentalene-6-yl; mono-, di- and tri-methyl-azapentalene-4-yl, 3-phenyl-2-5-dimethyl-thiapentalene-4-yl; 1-thio-3-phenyl-2,5-methyl-pentalene-6-yl The metal M is preferably Ti, Zr or Hf, more preferably it is Zr.

The substituents L are preferably the same and preferably they are $C_1$–$C_7$ alkyl groups, $C_6$–$C_{14}$ aryl groups and $C_7$–$C_{14}$ arylalkyl groups, optionally containing one or more Si or Ge atoms; more preferably, the substituents L are selected from the group consisting of methyl, ethyl, n-butyl, sec-butyl, phenyl, benzyl and —$CH_2Si(CH_3)_3$.

Non-limiting examples of metallocene compounds of formula (I) are:
dimethylsilanediylbis(indenyl)zirconium dimethyl,
dimethylsilanediylbis(2-methyl-4-phenylindenyl)zirconium dimethyl,
dimethylsilanediylbis(4-naphthylindenyl)zirconium dimethyl,
dimethylsilanediylbis(2-methylindenyl)zirconium dimethyl,
dimethylsilanediylbis(2-methyl-4-t-butylindenyl)zirconium dimethyl,
dimethylsilanediylbis(2-methyl-4-isopropylindenyl)zirconium dimethyl,
dimethylsilanediylbis(2,4-dimethylindenyl)zirconium dimethyl,
dimethylsilanediylbis(2-methyl-4,5-benzoindenyl)zirconium dimethyl,
dimethylsilanediylbis(2,4,7-trimethylindenyl)zirconium dimethyl,
dimethylsilanediylbis(2,4,6-trimethylindenyl)zirconium dimethyl,
dimethylsilanediylbis(2,5,6-trimethylindenyl)zirconium dimethyl,
methyl(phenyl)silanediylbis(2-methyl-4,6-diisopropylindenyl)zirconium dimethyl,
methyl(phenyl)silanediylbis(2-methyl-4-isopropylindenyl)zirconium dimethyl,
dimethylsilandiylbis (4,7-dimethylindenyl)zirconium dimethyl,
dimethylsilandiylbis (2-methyl-4,6-diisopropylindenyl)zirconium dimethyl,
dimethylsilanediyl(3-tert-butyl-cyclopentadienyl)(9-fluorenyl)zirconium dimethyl,
dimethylsilanediyl(3-isopropyl-cyclopentadienyl)(9-fluorenyl)zirconium dimethyl,
dimethylsilanediyl(3-methyl-cyclopentadienyl)(9-fluorenyl)zirconium dimethyl,
dimethylsilanediyl(3-ethyl-cyclopentadienyl)(9-fluorenyl)zirconium dimethyl,
dimethylsilanediylbis-6-(3-methylcyclopentadienyl-[1,2-b]-thiophene)dimethyl;
dimethylsilanediylbis-6-(4-methylcyclopentadienyl-[1,2-b]-thiophene)zirconium dimethyl;
dimethylsilanediylbis-6-(4-isopropylcyclopentadienyl-[1,2-b]-thiophene)zirconium dimethyl;
dimethylsilanediylbis-6-(4-ter-butylcyclopentadienyl-[1,2-b]-thiophene)zirconium dimethyl;
dimethylsilandiylbis-6-(3-isopropylcyclopentadienyl-[1,2-b]-thiophene)zirconium dimethyl;
dimethylsilandiylbis-6-(3-phenylcyclopentadienyl-[1,2-b]-thiophene)zirconium dimethyl;
dimethylsilandiylbis-6-(2,5-dimethyl-3-phenylcyclopentadienyl-[1,2-b]-thiophene)zirconium dimethyl;
dimethylsilandiylbis-6-[2,5-dimethyl-3-(2-methylphenyl)cyclopentadienyl-[1,2-b]-thiophene]zirconium dimethyl;
dimethylsilandiylbis-6-[2,5-dimethyl-3-(2,4,6-trimethylphenyl)cyclopentadienyl-[1,2-b]-thiophene]zirconium dimethyl;
dimethylsilandiylbis-6-[2,5-dimethyl-3-mesitylenecyclopentadienyl-[1,2-b]-thiophene]zirconium dimethyl;
dimethylsilandiylbis-6-(2,4,5-trimethyl-3-phenylcyclopentadienyl-[1,2-b]-thiophene)zirconium dimethyl;
dimethylsilandiylbis-6-(2,5-diethyl-3-phenylcyclopentadienyl-[1,2-b]-thiophene)zirconium dimethyl;
dimethylsilandiylbis-6-(2,5-diisopropyl-3-phenylcyclopentadienyl-[1,2-b]-thiophene)zirconium dimethyl;
dimethylsilandiylbis-6-(2,5-diter-butyl-3-phenylcyclopentadienyl-[1,2-b]-thiophene)zirconium dimethyl;
dimethylsilandiylbis-6-(2,5-ditrimethylsilyl-3-phenylcyclopentadienyl-[1,2-b]-thiophene)zirconium dimethyl;
dimethylsilandiylbis-6-(3-methylcyclopentadienyl-[1,2-b]-silole)zirconium dimethyl;
dimethylsilandiylbis-6-(3-isopropylcyclopentadienyl-[1,2-b]-silole)zirconium dimethyl;
dimethylsilandiylbis-6-(3-phenylcyclopentadienyl-[1,2-b]-silole)zirconium dimethyl;
dimethylsilandiylbis-6-(2,5-dimethyl-3-phenylcyclopentadienyl-[1,2-b]-silole)zirconium dimethyl;
dimethylsilandiylbis-6-[2,5-dimethyl-3-(2-methylphenyl)cyclopentadienyl-[1,2-b]-silole]zirconium dimethyl;
dimethylsilandiylbis-6-[2,5-dimethyl-3-(2,4,6-trimethylphenyl)cyclopentadienyl-[1,2-b]-silole]zirconium dimethyl;
dimethylsilandiylbis-6-[2,5-dimethyl-3-mesitylenecyclopentadienyl-[1,2-b]-silole]zirconium dimethyl;
dimethylsilandiylbis-6-(2,4,5-trimethyl-3-phenylcyclopentadienyl-[1,2-b]-silole)zirconium dimethyl;
[dimethylsilyl(2-methyl-1-indenyl)][(N-methyl-1,2-dihydrocyclopenta[2,1-b]indol-2-yl)]titanium dimethyl;
[dimethylsilyl(2-methyl-1-indenyl)][(6-methyl-N-methyl-1,2-dihydrocyclopenta[2,1-b]indol-2-yl)]titanium dimethyl;
[dimethylsilyl(2-methyl-1-indenyl)][(6-methoxy-N-methyl-1,2-dihydrocyclopenta[2,1-b]indol-2-yl)]titanium dimethyl;
[dimethylsilyl(2-methyl-1-indenyl)][(N-ethyl-1,2-dihydrocyclopenta[2,1-b]indol-2-yl)]titanium dimethyl;
[dimethylsilyl(2-methyl-1-indenyl)][(N-phenyl-1,2-dihydrocyclopenta[2,1-b]indol2-yl)]titanium dimethyl;
[dimethylsilyl(2-methyl-1-indenyl)][(6-methyl-N-phenyl-1,2-dihydrocyclopenta[2,1-b]indol2-yl)]titanium dimethyl;
[dimethylsilyl(2-methyl-1-indenyl)][(6-methoxy-N-phenyl-1,2-dihydrocyclopenta[2,1-b]indol2-yl)]titanium dimethyl;
[dimethylsilyl(2-methyl-1-indenyl)][(N-methyl-3,4-dimethyl-1,2-dihydrocyclopenta[2,1-b]indol-2-yl)]titanium dimethyl;
[dimethylsilyl(2-methyl-1-indenyl)][(N-ethyl-3,4-dimethyl-1,2-dihydrocyclopenta[2,1-b]indol-2-yl)]titanium dimethyl;
[dimethylsilyl(2-methyl-1-indenyl)][(N-phenyl-3,4-dimethyl-1,2-dihydroclopenta[2,1-b]indol-2-yl)]titanium dimethyl;

as well as the corresponding dibenzyl and diphenyl, compounds.

In an embodiment, the present invention relates to a process for preparing a silicon-bridged metallocene compound of formula (II):

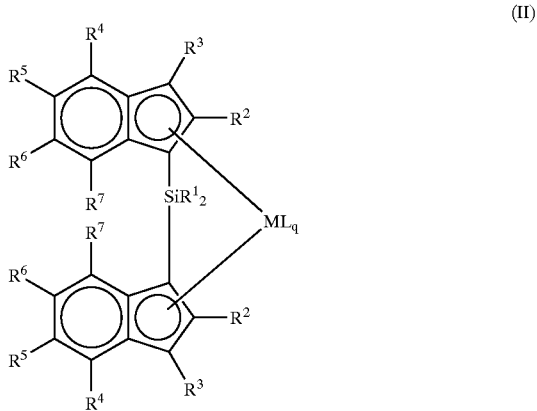

(II)

wherein:

M, L, q and $R^1$ have the meaning reported above;

$R^2$, equal to or different from each other, is a hydrogen atom or a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radical, optionally containing heteroatoms belonging to groups 13–17 of the Periodic Table of the Elements;

$R^3$, $R^4$, $R^5$, $R^6$ and $R^7$, equal to or different from each other, are hydrogen atoms or linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radicals, optionally containing heteroatoms belonging to groups 13–17 of the Periodic Table of the Elements; two vicinal $R^3$, $R^4$, $R^5$, $R^6$ and $R^7$ can also form one or more condensed 5 or 6 membered saturated or unsaturated rings optionally containing heteroatoms belonging to groups 13–16 of the Periodic Table of the Elements, said rings can bear alkyl substituents;

said process comprises the following steps:

a) reacting, at a temperature of between −10° C. and 70° C., a ligand of formula (III)

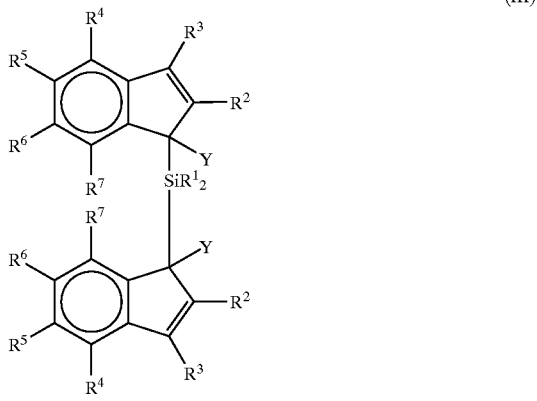

(III)

and/or one of its double bond isomers;
wherein $R^1$, $R^2$, $R^3$, $R^4$, $R^5$, $R^6$ and $R^7$ have the meaning described above; with about 2 molar equivalents of an alkylating agent of formula $TH_w$, $L_jB$ or LMgL', wherein L has the meaning reported above; T is lithium, sodium or potassium, H is an hydrogen atom, w is 0 or 1, when w is 0 the compound $TH_w$ is metallic lithium, sodium or potassium, when w is 1 the compound of formula $TH_w$ is an hydride of lithium, sodium or potassium, L' is an halogen atom selected from chlorine, bromine and iodine; B is an alkali or alkali-earth metal; and j is 1 or 2, j being equal to 1 when B is an alkali metal, and j being equal to 2 when B is an alkali-earth metal; the groups Y, the same or different from each other, are suitable leaving groups as reported above;

b) after the reaction has been completed, i.e. in a time ranging from 1 minute to 6 hours, preferably from 20 minutes to 5 hours, more preferably from 40 minutes to 5 hours, adding at least q molar equivalents, preferably at least 1+q molar equivalents, of a compound of formula $L_jB$ or LMgL'; and c) reacting, at a temperature between −10° C. and 70° C., the product obtained from step b) with at least 1 molar equivalent of a compound of formula $ML'_s$, wherein M have the meaning reported above; s is an integer corresponding to the oxidation state of the metal and ranges from 3 to 6; and L' is an halogen atom selected from chlorine, bromine and iodine.

In the compounds of formulas (II) and (III) $R^2$ is preferably a linear or branched, saturated or unsaturated $C_1$–$C_{20}$-alkyl radical;

$R^4$ is preferably a hydrogen atom, a $C_1$–$C_{20}$-alkyl radical, a $C_6$–$C_{20}$-aryl radical or form with $R^5$ a condensed benzene ring;

$R^5$ preferably is a hydrogen atom, a $C_1$–$C_{20}$-alkyl radical or form with $R^4$ a condensed benzene ring;

$R^6$ and $R^7$ are preferably hydrogen atoms or linear or branched, saturated or unsaturated $C_1$–$C_{20}$-alkyl radicals.

In a further embodiment, the present invention relates to a process for preparing a silicon-bridged metallocene compound of formula (IV):

(IV)

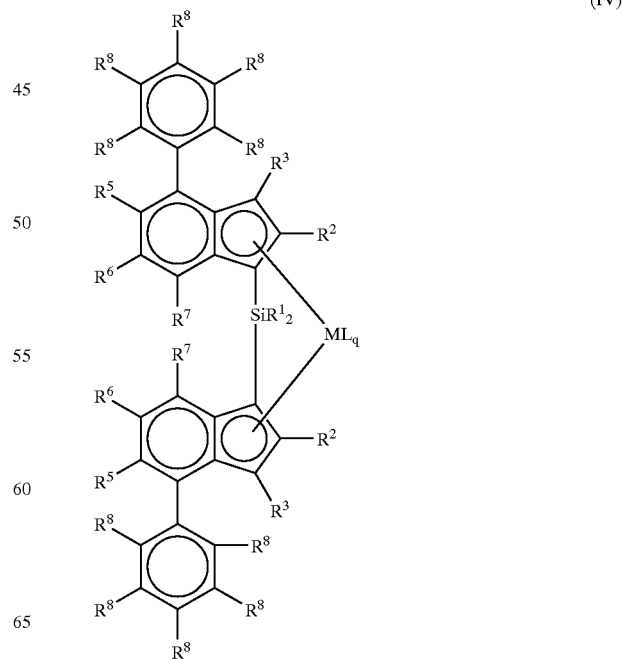

wherein:
M, L, q, $R^1$, $R^2$, $R^3$, $R^5$, $R^6$ and $R^7$ have the same meaning as above; and $R^8$, equal to or different from each other, is a hydrogen atom, or a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radical, optionally containing heteroatoms belonging to groups 13–17 of the Periodic Table of the Elements; preferably the $R^8$ substituent on position 4 of the phenyl ring is or a linear or branched, saturated or unsaturated $C_1$–$C_{20}$-alkyl, more preferably a tert-butyl radical; preferably the $R^8$ substituents on positions 2,3,4 and 5 are hydrogen atoms;

said process comprises the following steps;
a) reacting, at a temperature between –10° C. and 70° C., a ligand of formula (V)

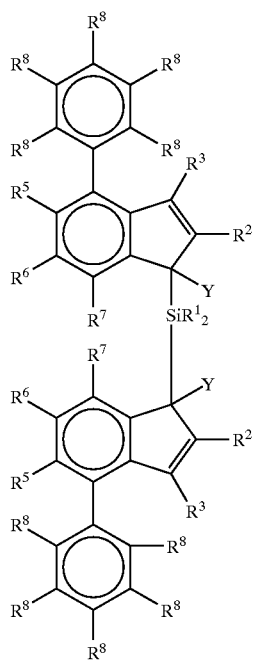

(V)

or one of its double bond isomers;
wherein $R^1$, $R^2$, $R^3$, $R^4$, $R^5$, $R^6$, $R^7$ and $R^8$ have the meaning described above;
with about 2 molar equivalents of an alkylating agent of formula $TH_w$, $L_jB$ or LMgL', wherein L has the meaning reported above; T is lithium, sodium or potassium, H is an hydrogen atom, w is 0 or 1, when w is 0 the compound $TH_w$ is metallic lithium, sodium or potassium, when w is 1, the compound of formula $TH_w$ is an hydride of lithium, sodium or potassium, L' is an halogen atom selected from chlorine, bromine and iodine; B is an alkali or alkali-earth metal; and j is 1 or 2, j being equal to 1 when B is an alkali metal, and j being equal to 2 when b is an alkali-earth metal; the groups Y, the same or different from each other, are suitable leaving groups;

b) after the reaction has been completed, i.e. in a time ranging from 1 minute to 6 hours, preferably from 20 minutes to 5 hours, more preferably from 40 minutes to 5 hours, adding at least q molar equivalents, preferably at least 1+q molar equivalents, of a compound of formula $L_jB$ or LMgL'; and c) reacting, at a temperature between –10° C. and 70° C., the product obtained from step b) with at least 1 molar equivalent of a compound of formula $ML'_s$, wherein M have the meaning reported above; s is an integer corresponding to the oxidation state of the metal and ranges from 3 to 6; and L' is an halogen atom selected from chlorine, bromine and iodine.

The metallocene compounds of formulas (I), (II) and (IV) can be finally isolated from the reaction mixture obtained in step c) and optionally purified according to standard procedures. Said process allows to obtain the cyclopentadienyl metallocene compounds of formula (I) in very high yields, by means of a very practical and convenient one-pot reaction.

The leaving group Y is preferably an hydrogen atom a —$SiR_3$ or —$SnR_3$ group, wherein the groups R are linear or branched, saturated or unsaturated $C_1$–$C_{20}$-allyl, $C_3$–$C_{20}$-cycloalkyl, $C_6$–$C_{20}$-aryl, $C_7$–$C_{20}$-alkylaryl or $C_7$–$C_{20}$-arylalkyl radicals; more preferably Y is a hydrogen atom. In the reactant $ML'_s$, the metal M is preferably Ti, Zr or Hf, and the substituents L' are preferably the same and are chlorine atoms; the variable s ranges from 3 to 6 and corresponds to the oxidation state of the metal M; examples of compounds $ML_s$ are $ZrCl_4$, $ZrBr_4$, $ZrF_4$, $HfCl_4$, $HfBr_4$, $HfF_4$, $TiCl_4$, $TiBr_4$ and $TiF_4$. Compounds of formula $ML_s$ can be used in the form of a stabilized derivative, such as an etherate complex. Examples of compound of formula $TH_w$ are metallic sodium or potassium, sodium hydride and potassium hydride. In the $L_jB$ and LMgL' alkylating agents, L is preferably a $C_1$–$C_7$ alkyl group, a $C_6$–$C_{14}$ aryl group, or a $C_7$–$C_{14}$ arylalkyl group, optionally substituted with Si or Ge, and more preferably L is selected from the group consisting of methyl, ethyl, n-butyl, sec-butyl, phenyl, benzyl and —$CH_2Si(CH_3)_3$; even more preferably, L is methyl. In the compound $L_jB$, B is an alkali or alkali-earth metal, and preferably B is Li or Mg; j can be 1 or 2, as already reported.

The compound LMgL' is a Grignard reagent, wherein Mg is magnesium and L and L' have the meanings reported above; L' is preferably Cl or Br. The alkylating agents used in steps a) and b) can be the same or different. For example, butyllithium or sodium hydride can be used in step a) and methyl lithium can be used in step b). This gives rise to a further advantage for the reason that it is possible to use stronger and sometimes less expensive reagents in step a) without influencing the choice of the substituents L in step b). According to an embodiment of the process of the invention, said alkylating agent is methyllithium.

According to an embodiment, the process of the invention is carried out in an aprotic solvent, either polar or apolar; said aprotic solvent is preferably an aromatic or aliphatic hydrocarbon or an ether. Steps a) and b) are more preferably carried out in etherate solvents or mixtures of etherate solvents with hydrocarbons. Examples of etherate solvents are diethylether, tetrahydrofuran diisopropylether, dioxane, dimetoxyethane or mixtures thereof. In step c) the compound $ML'_s$ can be added as such, as a suspension or solution in a hydrocarbon solvent, or as a solution or a suspension in an etherate solvent. According to another embodiment of the process of the invention, in step a) the starting ligands are previously dissolved in an aprotic solvent and to the resulting solution about 2 equivalents of the alkylating agent $TH_w$, $L_jB$ or LMgL' are added; this addition is preferably carried out at a temperature ranging from –5° C. to +30° C., and more preferably from 0° C. to 25° C., over a period of 5–45 minutes, and more preferably of 10–20 minutes. The alkylating agent is preferably added slowly in the form of a solution in one of the above mentioned aprotic solvents. The thus obtained reaction mixture is preferably allowed to react, under stirring, for a period ranging from 1 minute to 6 hours, and more preferably from 20 minutes to 5 hours, at a temperature preferably comprised between −5° C. and +55° C., and more preferably at a temperature between 0° C. and 50° C. After the reaction has been completed, i.e. all the cyclopentadienyl ligand reacted with the alkylating agent, at least q equivalents preferably q+1 equivalents of said alkylating agent are added at a temperature comprised between −10° C. and +70° C., preferably at a temperature between −5° C. and 55° C. Then the mixture obtained from step b) is preferably heated at a temperature comprised between 0° C. and 60° C., and more preferably between 20° C. and 50° C. Afterwards the compound $ML'_s$ is quickly added to the mixture, in the form of a solution or suspension in one of the above mentioned aprotic solvents, preferably toluene. The reaction mixture is then allowed to react for a period ranging from 10 minutes to 36 hours, and more preferably from 1 hour to 18 hours, at a temperature comprised between 0° C. and 60° C., and more preferably between 20° C. and 50° C. The thus obtained metallocene compounds of formula (I) can be isolated according to customary procedures. Mixtures of racemic and meso isomers can be obtained and pure isomers can be separated in high yields by using standard procedures. The metallocene compounds obtained with the process according to the present invention can be used as catalyst for the homo or co-polymerization of olefins, in particular of α-olefins of formula $CH_2=CHT$ wherein T is hydrogen or a $C_1-C_{20}$ alkyl, such as ethylene propylene, 1-butene, 1-pentene, 4-methyl-1-pentene, 1-hexene and 1-octene, in combination with alumoxanes and/or organometallic aluminum compounds. They can be advantageously used for the production of polyethylene, especially HDPE and LLDPE, isotactic, syndiotactic or atactic polypropylene. Furthermore, they can be used in the copolymerization of ethylene with cycloolefins, such as cyclopentene, cyclohexene, norbornene and 4,6-dimethyl-1-heptene, or in ethylene copolymerization with polyenes, such as 1,4-hexadiene, isoprene, 1,3-butadiene, 1,5-hexadiene and 1,6-heptadiene. Finally, they can be advantageously used in olefin oligomerization and hydrogenation reactions. The above metallocenes form suitable polymerization catalytic systems in association with alumoxanes of formula:

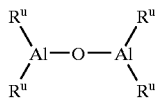

wherein the substituents R" can be $C_1-C_{10}$ alkyl, alkenyl or alkylaryl radicals, optionally containing one or more Si or Ge; or in association with an organometallic aluminum compound of formula $AlR''_{3-z}H_z$, wherein R" can be $C_1-C_{10}$ alkyl, alkenyl or alkylaryl radicals, optionally containing one or more Si or Ge atoms, and z ranges from 0 to 2 being also a non integer number, and water. Particularly suitable alumoxanes, acting as cocatalysts with the above metallocenes, are methylalumoxane (MAO), tris(2-methyl-propyl)alumoxane (TIBAO) and 2,4,4-trimethyl-pentylalumoxane (TIOAO). Non-limiting examples of organometallic aluminum are trimethylaluminum (TMA), tris(2,4,4-trimethyl-pentyl)aluminum (TIOA), tris(2-methyl-propyl)aluminum (TIBA), tris(2,3,3-trimethyl-butyl)aluminum, tris(2,3-dimethyl-hexyl)aluminum, tris(2,3-dimethyl-butyl) aluminum, tris(2,3-dimethyl-pentyl)aluminum, tris(2,3-dimethyl-heptyl)aluminum, tris(2-methyl-3-ethyl-pentyl) aluminum and tris(2-ethyl-3,3-dimethyl-butyl). Other suitable cocatalysts are compounds capable of forming a metallocene cation, having formula $Y^+Z^-$, wherein $Y^+$ is a Brønsted acid (such as $Ph_3C^+$ or $HN^+(n\text{-}Bu)_3$) and $Z^-$ is a non-coordinating anion (such as $[B(C_6F_5)_4]^-$=tetrakis-pentafluorophenyl borate), able to stabilize the active catalyst species and sufficiently labile to be displaced by an olefinic substrate. The above catalysts can be used on inert supports, such as silica, alumina, styrene/divinylbenzene copolymers, polyethylene or polypropylene. Those supported catalysts are particularly suitable in gas phase polymerizations.

The polymerization processes can be carried out in liquid phase, optionally in the presence of an inert hydrocarbon solvent either aromatic (e.g. toluene) or aliphatic (e.g. propane, hexane, heptane, isobutane, cyclohexane and 2,2,4-trimethylpentane). The polymerization temperature generally ranges from about 0° C. to about 250° C., and preferably from 20 to 150° C.

The following examples are given for illustrative and not limitative purposes.

EXAMPLES

General Procedures and Characterizations

All operations were performed under nitrogen by using conventional Schlenk-line techniques. Solvents were purified by degassing with $N_2$ and passing over activated (8 hours, $N_2$ purge, 300° C.) $Al_2O_3$, and stored under nitrogen. MeLi (Acros or Aldrich or Fluka) and $ZrCl_4$ (Aldrich) were used as received. The exact concentration of the commercial MeLi solution in diethyl ether was determined by a potentiometric titration with HCl of 2 mL of MeLi solution, previously treated with 20 mL of deionized water to form LiOH. Bis(2-methyl-4-phenyl-indenyl)dimethylsilane was prepared by following the procedure described in Example A of the European Patent Application No. 0576970 A1. $Me_2SiCl_2$ (Aldrich) was used as received, while technical indene (Aldrich) was purified by passing over activated $Al_2O_3$. The proton spectra of ligands and metallocenes were obtained on a Bruker DPX 200 spectrometer operating in the Fourier transform mode at room temperature at 200.13 MHz. The samples were dissolved in $CD_2Cl_2$ or $C_6D_6$. $C_6D_6$ (Aldrich, 99.6 atom % D) was stored over molecular sieves (4–5 Å), while $CD_2Cl_2$ (Aldrich, 99.8 atom % D) was used as received. Preparation of the samples was carried out under nitrogen using standard inert atmosphere techniques. The residual peak of $CHDCl_2$ or $C_6HD_5$ in the $^1H$ spectra (5.35 ppm and 7.15 ppm, respectively) was used as a reference. Proton spectra were acquired with a 15° pulse and 2 seconds of delay between pulses; 32 transients were stored for each spectrum. The element contents were determined by different analytical techniques: for C—H by Elemental Analyser (CHNS-O), a Carlo Erba instrument mod. EA 1108 (applied directly on the sample); for Zr by Inductively Coupled Plasma (ICP) on an ARL 3580 instrument, after strong acidic decomposition of the sample.

Example 1

Synthesis of $Me_2Si(2\text{-}Me\text{-}4\text{-}PhInd)_2ZrMe_2$

A 1.6 M MeLi solution in ethyl ether (23.7 mL, 37.92 mmol, MeLi:$Me_2Si(2\text{-}Me\text{-}4\text{-}Ph\text{-}Ind)_2$=2.10:1) was added dropwise at room temperature to an orange solution of 8.45 g of bis(2-methyl-4-phenyl-indenyl)dimethylsilane (MW=468.72, 18.03 mmol) in 7.6 mL of THF and 140 mL of toluene. At the end of the addition, the reaction mixture was stirred for 1 h at room temperature and then for 1 h at 40° C. Additional 35.3 mL of MeLi 1.6 M in Et$_2$O (56.48 mmol, total eq. of MeLi=5.24 with respect to the starting ligand) were added 7 minutes before the metallation. Then the dilithium salt solution (containing an excess of MeLi) was added at 45° C. in 20 min to a slurry of ZrCl$_4$ (4.20 g, MW=233.03, 18.02 mmol, ZrCl$_4$:Me$_2$Si(2-Me-4-Ph-Ind)$_2$=1.0:1) in 160 mL of toluene, previously heated at 45° C. too. At the end of the addition a dark brown (almost black) suspension was obtained. After 10 min stirring a $^1$H NMR analysis in CD$_2$Cl$_2$ showed complete conversion of the starting ligand to the dimethyl compound. The reaction mixture was concentrated to a final volume of 40 mL and under stirring filtered on a G3 frit. The residue was extracted at 60° C. with toluene until the solution resulted to be colourless. The extract in toluene was dried under reduced pressure to give a yellow powder as product. Yield 70%.

Anal. Calcd. for C$_{36}$H$_{36}$SiZr: C, 73.54%; H, 6.17%; Si, 4.78%; Zr, 15.51%; Found: C, 73.2%; H, 5.9%; Zr, 14.7%.

Comparative Example 2

Synthesis of Me$_2$Si(2-Me-4-PhInd)$_2$ZrMe$_2$

A 1.6 M MeLi solution in ethyl ether (7.60 mL, 12.16 mmol, MeLi:Me$_2$Si(2-Me-4-Ph-Ind)$_2$=4:1) was added dropwise at room temperature to a yellow solution of 1.42 g of bis(2-methyl-4-phenyl-indenyl)dimethylsilane (MW=468.72, 3.03 mmol) in 32 mL of i-Pr$_2$O and 30 mL of toluene. During the addition the colour turned from yellow to orange and a light exothermicity (+4° C.) was observed. The dilithium salt solution containing a MeLi excess was stirred for 1 h at room temperature, then a slurry of ZrCl$_4$ (0.70 g, MW=233.03, 3.00 mmol, ZrCl$_4$:Me$_2$Si(2-Me-4-Ph-Ind)$_2$=1:1) in 10 mL of toluene was added at the same temperature. After 2 h stirring the resulting brown suspension was analysed by $^1$H NMR in CD$_2$Cl$_2$, which showed mainly formation of Me$_2$Si(2-Me-4-Ph-Ind)$_2$ZrCl$_2$ and only traces of the desired dimethyl compound.

This example shows that if step a) and b) of the present invention are carried out in one sequence it is not possible to achieve the desired product.

Comparative Example 3

Synthesis of Me2Si(2-Me4-PhInd)$_2$ZrMe$_2$

A 1.72 M MeLi solution in ethyl ether (6.25 mL, 10.75 mmol, MeLi:Me$_2$Si(2-Me-4-Ph-Ind)$_2$=4:1) was added dropwise at 0° C. to a yellow solution of 1.26 g of bis(2-methyl-4-phenyl-indenyl)dimethylsilane (MW=468.72, 2.69 mlmol) in 15 mL of i-Pr$_2$O, 5 mL of THF and 10 mL of toluene. During the addition the colour turned from yellow to orange-brownish. The dilithium salt solution containing a MeLi excess was allowed to warm up to room temperature and stirred for 1 h. Then a slurry of ZrCl$_4$ (0.63 g, MW=233.03, 2.70 mmol, ZrCl$_4$:Me$_2$Si(2-Me-4-Ph-Ind)$_2$=1:1) in 15 mL of toluene was added at room temperature. After 1 h stirring the resulting brown suspension was analysed by $^1$H NMR in CD$_2$Cl$_2$, which showed mainly formation of Me$_2$Si(2-Me-4-Ph-Ind)$_2$ZrCl$_2$ and only traces of the desired dimethyl compound. This example shows that, if step b) of the present invention is carried out without allowing the reaction of step a) to be completed, it is not possible to achieve the desired product even if a different solvent is used.

Comparative Example 4

Synthesis of Me$_2$Si(2-Me-4-PhInd)$_2$ZrMe$_2$

A 1.6 M MeLi solution in ethyl ether (6.70 mL, 10.72 mmol, MeLi:Me$_2$Si(2-Me-4-Ph-Ind)$_2$=2.01:1) was added dropwise at room temperature to a suspension of 2.50 g of bis(2-methyl-4-phenyl-indenyl)dimethylsilane (MW=468.72, 5.33 mmol) in 5.0 mL of iPr$_2$O and 35 mL of toluene. At the end of the addition, the reaction mixture was heated at 40° C. for 1.5 h, then the resulting orange solution was added of additional 8.4 mL of MeLi 1.6 M in Et$_2$O (13.44 mmol, total eq. of MeLi=4.5 with respect to the starting ligand). After 5 min the dilithium salt solution (containing an excess of MeLi) kept at 45° C. was added in 15 min to a slurry of ZrCl$_4$ (1.25 g, MW=233.03, 5.36 mmol, ZrCl$_4$:Me$_2$Si(2-Me-4-Ph-Ind)$_2$=1.0:1) in 30 mL of toluene, at 75° C. At the end of the addition a dark brown (almost black) suspension was obtained. After 5 min stirring a $^1$H NMR analysis in CD$_2$Cl$_2$ showed traces of the dimethyl compound.

This example shows that, if step b) of the present invention is carried out without allowing the reaction of step a) to be completed, and if the temperature of step c) is out of the claimed range it is not possible to achieve the desired product.

Example 5

Synthesis of Me$_2$Si(2-Me-Ind)$_2$ZrMe$_2$

A 3.05 M MeLi solution in diethoxymethane (8.5 mL, 25.92 mmol, MeLi:Me$_2$Si(2-MeIndH)$_2$=2.05:1) was added dropwise at 0° C. to a solution of 4.00 g of bis(2-methyl-indenyl)dimethylsilane (MW=316.52, 12.64 mmol) in 40 mL of THF. At the end of the addition, the reaction mixture was allowed to warm up to room temperature and stirred for 1 h and 30 min. Additional 8.5 mL of MeLi 3.05 M in diethoxymethane (25.92 mmol, total eq. of MeLi=4.10 with respect to the starting ligand) were added dropwise at 0° C. few minutes before the metallation. Then a slurry of ZrCl$_4$ (2.95 g, MW=233.03, 12.66 mmol, ZrCl$_4$:Me$_2$Si(2-MeIndH)$_2$=1.00:1) in 40 mL of toluene was added at 0° C. to the dilithium salt solution (containing an excess of MeLi). At the end of the addition, the reaction mixture was allowed to warm up to room temperature and heated at 40° C. for 1 h and 30 min with final formation of a dark brown (almost black) suspension. A $^1$H NMR analysis in CD$_2$Cl$_2$ showed nearly complete conversion of the starting ligand to the dimethyl compound. The solvents were then removed under reduce pressure giving a black residue. The latter was extracted in a Soxhlet apparatus with 150 mL of pentane. The filtrate was evaporated to dryness under reduced pressure to give 3.60 g of a yellow powder (65.2% metal-based yield), which was characterized by $^1$H NMR as spectroscopically pure Me$_2$Si(2-MeInd)$_2$ZrMe$_2$.

$^1$H-NMR (CD$_2$Cl$_2$, δ, ppm, rac): −1.28 (s, 6H, Zr—CH$_3$); 1.12 (s, 6H, Si—CH$_3$); 2.09 (s, 6H, 2-CH$_3$); 6.78 (s, H3, 2H); 6.95 (ddd, H5 or H6, 2H, J=1.57, 6.65, 8.61 Hz); 7.28 (ddd, H6 or H5, 2H, J=1.57, 6.65, 8.61 Hz); 7.53–7.59 (m, Ar, 4H).

$^1$H-NMR (CD$_2$Cl$_2$, δ, ppm, meso): −2.35 (s, 3H, Zr—CH$_3$); 0.02 (s, 3H, Zr—CH$_3$); 1.04 (s, 3H, Si—CH$_3$); 1.23 (s, 3H, Si—CH$_3$); 2.35 (s, 6H, 2-CH$_3$); 6.67 (ddd, H5 or H6, 2H, J=1.57, 6.65, 8.61 Hz); 6.80 (s, H3, 2H); 7.05 (ddd, H6 or H5, 2H, J=1.57, 6.65, 8.61 Hz); 7.38–7.53 (m, Ar, 4H).

13

Comparative Example 6

Synthesis of Me$_2$Si(2-Me-Ind)$_2$ZrMe$_2$

A titrated 1.66 M MeLi solution in Et$_2$O (22.6 mL, 37.52 mmol, MeLi:Me$_2$Si(2-MeIndH)$_2$=4:1) was added dropwise at room temperature to a solution of 3.00 g of bis(2-methyl-indenyl)dimethylsilane MW=316.52, 98.9% by GC-MS, 9.37 mmol) in 40 mL of Et$_2$O. At the end of the addition, the reaction mixture was stirred for 3 h with final formation of a white suspension. Then a slurry of ZrCl$_4$ (2.19 g, MW=233.03, 9.40 mmol, ZrCl$_4$/Me$_2$Si(2-MeIndH)$_2$=1:1) in 60 mL of toluene was quickly added to the lithium salt suspension, previously cooled to 16° C. by a water bath. During the addition the colour turned from white to yellow and a light exothermicity (+5° C.÷6° C.) was observed. After 1 h stirring at room temperature a $^1$H NMR in C$_6$D$_6$ showed the presence of a large amount of polymeric by-products and only a small amount of the desired dimethyl metallocene.

This example shows that, if step b) of the present invention is carried out without allowing the reaction of step a) to be completed, it is not possible to achieve the desired product.

The invention claimed is:

1. A process for preparing silicon-bridged metallocene compounds of formula (I):

(I)

wherein (SiR$^1_2$) is a divalent group bridging the two Cp rings, the R$^1$ groups, equal to or different from each other, are hydrogen atoms, or linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl or C$_7$–C$_{20}$ arylalkyl groups, two R$^1$ can optionally join to form a 3–7 membered ring;

Cp, equal to or different from each other, is a substituted or unsubstituted cyclopentadienyl group, optionally condensed to one or more substituted or unsubstituted, saturated, unsaturated or aromatic rings, containing from 4 to 6 carbon atoms, optionally containing one or more heteroatoms;

M is a transition metal belonging to group 3, 4, 5, 6 or to the lanthanide or actinide groups of the Periodic Table of the Elements (IUPAC version);

the substituents L, equal to or different from each other, are monoanionic sigma ligands selected from the group consisting of linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl and C$_7$–C$_{20}$ arylalkyl groups, optionally containing one or more Si or Ge atoms;

q is an integer ranging from 0 to 2, being equal to the oxidation state of the metal M minus 2;

said process comprises the following steps:

a) reacting, at a temperature of between –10° C. and 70° C., a ligand of formula (Y-Cp)(SiR$^1_2$)(Cp-Y) with about 2 molar equivalents of an alkylating agent of formula TH$_w$, L$_j$B or LMgL', wherein T is lithium, sodium or potassium, H is an hydrogen atom, w is 0 or 1, when w is 0 the compound TH$_w$ is metallic lithium, sodium or potassium, when w is 1 the compound of formula TH$_w$ is an hydride of lithium, sodium or potassium; L' is an halogen atom selected from chlorine, bromine and iodine; B is an alkali or alkali-earth metal; and j is 1 or 2, j being equal to 1 when B is an alkali metal, and j being equal to 2 when B is an alkali-earth metal; the groups Y, the same or different from each other, are suitable leaving groups;

14 b) after the reaction has been completed, adding at least q molar equivalents of an alkylating agent of formula L$_j$B or LMgL'; and c) reacting, at a temperature of between –10° C. and 70° C., the product obtained from step b) with at least 1 molar equivalent of a compound of formula ML'$_s$, wherein s is an integer corresponding to the oxidation state of the metal and ranges from 3 to 6; and L' is an halogen atom selected from chlorine, bromine and iodine.

2. The process according to claim 1, for preparing a silicon-bridged metallocene compound of formula (II):

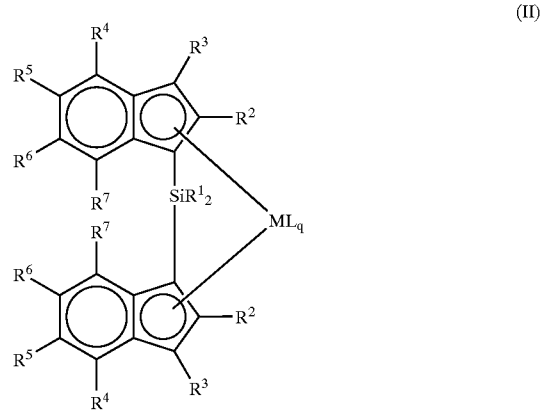

(II)

wherein:

R$^2$, equal to or different from each other, are hydrogen atoms or linear or branched, saturated or unsaturated C$_1$–C$_{20}$-alkyl, C$_3$–C$_{20}$-cycloalkyl, C$_6$–C$_{20}$-aryl, C$_7$–C$_{20}$-alkylaryl or C$_7$–C$_{20}$-arylalkyl radicals, optionally containing heteroatoms belonging to groups 13–17 of the Periodic Table of the Elements;

R$^3$, R$^4$, R$^5$, R$^6$ and R$^7$, equal to or different from each other, are hydrogen atoms or linear or branched, saturated or unsaturated C$_1$–C$_{20}$-alkyl, C$_3$–C$_{20}$-cycloalkyl, C$_6$–C$_{20}$-aryl, C$_7$–C$_{20}$-alkylaryl or C$_7$–C$_{20}$-arylalkyl radicals, optionally containing heteroatoms belonging to groups 13–17 of the Periodic Table of the Elements; two vicinal R$^3$, R$^4$, R$^5$, R$^6$ and R$^7$ can also form one or more condensed 5 or 6 membered saturated or unsaturated rings optionally containing heteroatoms belonging to groups 13–16 of the Periodic Table of the Elements, said rings can bear alkyl substituents;

said process comprises the following steps:

a) reacting, at a temperature of between –10° C. and 70° C., a ligand of formula (III)

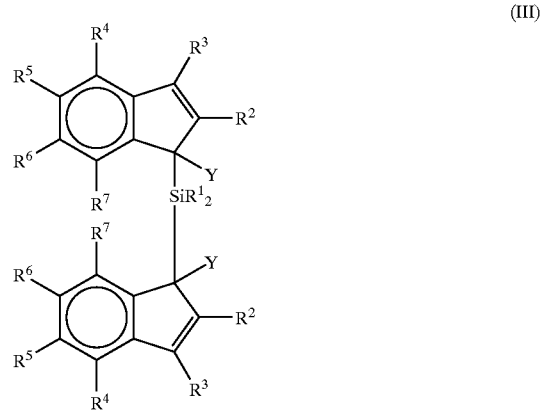

(III)

or one of its double bond isomers;
with about 2 molar equivalents of an alkylating agent of formula $TH_w$, $L_jB$ or $LMgL'$, wherein T is lithium, sodium or potassium, H is an hydrogen atom, w is 0 or 1, when w is 0 the compound $TH_w$ is metallic lithium, sodium or potassium, when w is 1 the compound of formula $TH_w$ is an hydride of lithium, sodium or potassium, L' is an halogen atom selected from chlorine, bromine and iodine; B is an alkali or alkali-earth metal; and j is 1 or 2, j being equal to 1 when B is an alkali metal, and j being equal to 2 when B is an alkali-earth metal; the groups Y, the same or different are suitable leaving groups;

b) after the reaction has been completed, adding at least q molar equivalents, of a compound of formula $L_jB$ or $LMgL'$; and c) reacting, at a temperature of between $-10°$ C. and $70°$ C., the product obtained from step b) with at least 1 molar equivalent of a compound of formula $ML'_s$, wherein s is an integer corresponding to the oxidation state of the metal and ranges from 3 to 6; and L' is an halogen atom selected from chlorine, bromine and iodine.

3. The process according to claim 1, for preparing a silicon-bridged metallocene compound of formula (IV):

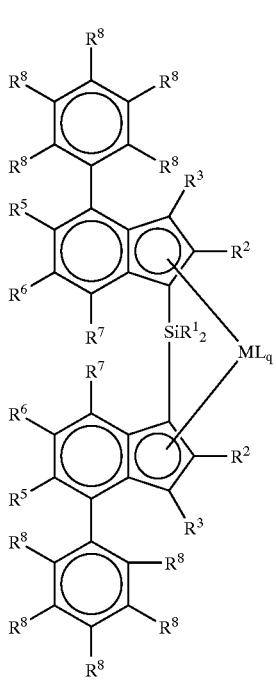

(IV)

wherein:

$R^2$, equal to or different from each other, are hydrogen atoms or linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radicals, optionally containing heteroatoms belonging to groups 13–17 of the Periodic Table of the Elements;

$R^3$, $R^4$, $R^5$, $R^6$ and $R^7$, equal to or different from each other, are hydrogen atoms or linear or branched, saturated or unsaturated $C_1$–$C_{20}$-alkyl, $C_3$–$C_{20}$-cycloalkyl, $C_6$–$C_{20}$-aryl $C_7$–$C_{20}$-alkylaryl or $C_7$–$C_{20}$-arylalkyl radicals, optionally containing heteroatoms belonging to groups 13–17 of the Periodic Table of the Elements;

two vicinal $R^3$, $R^4$, $R^5$, $R^6$ and $R^7$ can also form one or more condensed 5 or 6 membered saturated or unsaturated rings optionally containing heteroatoms belonging to groups 13–16 of the Periodic Table of the Elements, said rings can bear alkyl substituents;

and $R^8$ is a hydrogen atom, or a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radical, optionally containing heteroatoms belonging to groups 13–17 of the Periodic Table of the Elements;

said process comprises the following steps;

a) reacting, at a temperature of between $-10°$ C. and $70°$ C., a ligand of formula (V)

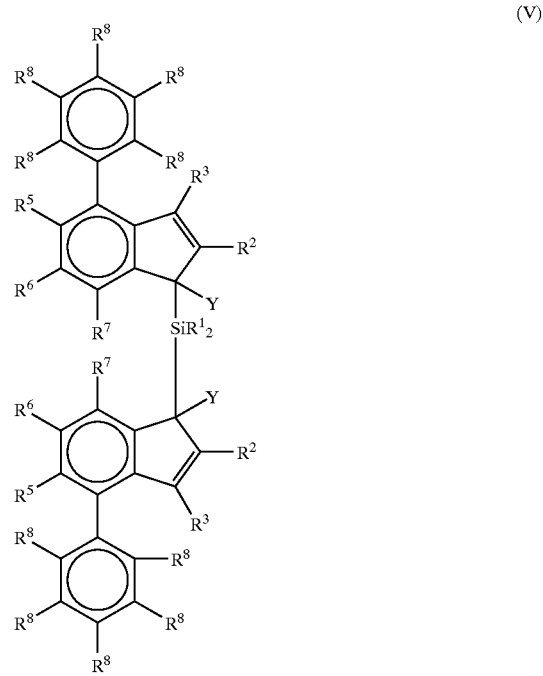

(V)

or one of its double bond isomers;

with about 2 molar equivalents of an alkylating agent of formula $TH_w$, $L_jB$ or $LMgL'$, wherein T is lithium, sodium or potassium, H is an hydrogen atom, w is 0 or 1, when w is 0 the compound $TH_w$ is metallic lithium, sodium or potassium, when w is 1 the compound of formula $TH_w$ is an hydride of lithium, sodium or potassium, L' is an halogen atom selected from chlorine, bromine and iodine;

B is an alkali or alkali-earth metal; and j is 1 or 2, j being equal to 1 when B is an alkali metal, and j being equal to 2 when B is an alkali-earth metal; the groups Y, the same or different from each other, are suitable leaving groups;

b) after the reaction has been completed, adding at least q molar equivalents of a compound of formula $L_jB$ or $LMgL'$; and c) reacting, at a temperature of between $-10°$ C. and $70°$ C., the product obtained from step b) with at least 1 molar equivalent of a compound of formula $ML'_s$, wherein s is an integer corresponding to the oxidation state of the metal and ranges from 3 to 6; and L' is an halogen atom selected from chlorine, bromine and iodine.

4. The process according to claim 1 wherein step b) is carried out in a time ranging from 1 minute to 6 hours after step a).

5. The process according to claim 1 wherein Y is a hydrogen atom or a —SiR$_3$ or —SnR$_3$ group, wherein the groups R are linear or branched saturated or unsaturated C$_1$–C$_{20}$-alkyl, C$_3$–C$_{20}$-cycloalkyl, C$_6$–C$_{20}$-aryl, C$_7$–C$_{20}$-alkylaryl or C$_7$–C$_{20}$-arylalkyl radicals.

6. The process according to claim 1 wherein the metal M is Ti, Zr or Hf.

7. The process according to claim 1 wherein the compounds ML$_s$ are ZrCl$_4$, ZrBr$_4$, ZrF$_4$, HfCl$_4$, HfBr$_4$, HfF$_4$, TiCl$_4$, TiBr$_4$ and TiF$_4$.

8. The process according to claim 1 wherein in step b) at least 1+q molar equivalents of a compound of formula L$_j$B or LMgL' is added.

9. The process according to claim 1 wherein step a) and b) are carried out at a temperature ranging from −5° C. and +55° C.

10. The process according to claim 1 wherein step c) is carried out at a temperature ranging from 0° C. and 60° C.

* * * * *